(12) United States Patent  (10) Patent No.: US 8,225,648 B2
Nelson  (45) Date of Patent: Jul. 24, 2012

(54) PARTICULATE MATTER SENSOR (75) Inventor: Charles Scott Nelson, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 136 days.

(21) Appl. No.: 12/782,123

(22) Filed: May 18, 2010

(65) Prior Publication Data
US 2011/0232268 A1 Sep. 29, 2011

Related U.S. Application Data (60) Provisional application No. 61/317,003, filed on Mar. 24, 2010.

(51) Int. Cl.
*G01N 7/00* (2006.01)
*G01M 15/00* (2006.01)
(52) U.S. Cl. .................... 73/114.71; 73/23.31
(58) Field of Classification Search ............. 73/23.31, 73/23.33, 114.71, 114.73
See application file for complete search history.

(56) References Cited

U.S. PATENT DOCUMENTS

| | | | | |
|---|---|---|---|---|
| 4,240,890 A * | 12/1980 | Watanabe et al. | ............. | 204/410 |
| 4,986,892 A * | 1/1991 | Kato et al. | ............. | 204/427 |
| 5,817,920 A * | 10/1998 | Kuisell et al. | ............. | 73/23.31 |
| 6,202,469 B1 * | 3/2001 | Nakamura et al. | ............. | 73/23.31 |
| 6,401,521 B1 * | 6/2002 | Nelson | ............. | 73/31.05 |
| 6,551,498 B2 * | 4/2003 | Nelson | ............. | 205/784.5 |
| 7,739,898 B2 * | 6/2010 | Shaddock et al. | ............. | 73/31.05 |
| 2003/0121782 A1 * | 7/2003 | Atsumi et al. | ............. | 204/424 |
| 2006/0243027 A1 * | 11/2006 | Nelson et al. | ............. | 73/23.31 |
| 2006/0289308 A1 * | 12/2006 | Shaddock et al. | ............. | 204/424 |
| 2008/0282769 A1 | 11/2008 | Nelson | | |
| 2008/0283398 A1 | 11/2008 | Nelson et al. | | |
| 2009/0056416 A1 | 3/2009 | Nair et al. | | |
| 2009/0139081 A1 | 6/2009 | Nelson | | |

* cited by examiner

*Primary Examiner* — Freddie Kirkland, III
(74) *Attorney, Agent, or Firm* — Thomas N. Twomey (57) ABSTRACT

A particulate matter sensor is provided for sensing particulate matter present in exhaust gases in a conduit. The particulate matter sensor includes a sensing element with a sensing face which extends into the exhaust conduit and provides a signal indicative of the amount of particulate matter detected in the exhaust conduit. An inner shield is provided to surround the sensing face and includes an inner shield inlet for admitting exhaust gases therein to be sensed. An outer shield surrounds a portion of the inner shield and defines an outer shield chamber extending axially beyond the inner shield. The outer shield has an outer shield inlet passage to receive exhaust gasses from the conduit. Exhaust gases enter the inner shield from the outer shield chamber through the inner shield inlet.

33 Claims, 6 Drawing Sheets

PARTICULATE MATTER SENSOR

CROSS-REFERENCE TO RELATED APPLICATIONS

This application claims the benefit of U.S. provisional patent application Ser. No. 61/317,003 filed Mar. 24, 2010, the disclosure of which is hereby incorporated by reference in its entirety.

TECHNICAL FIELD OF INVENTION

The present invention relates to particulate matter sensors for sensing the amount of particulate matter or soot in the exhaust conduit of a diesel engine; and more particularly to a sensor element shield arrangement for such particulate matter sensors.

BACKGROUND OF INVENTION

Knowing the amount of particulate matter or soot present in the exhaust stream of a diesel engine is important for determining the operational state of an exhaust gas treatment device, for example, a diesel particulate filter. A particulate matter sensor is often placed in the exhaust conduit in order to sense the amount of particulate matter present in the exhaust stream. The amount of particulate matter sensed by the particulate matter sensor may then be used, for example, to determine if the diesel particulate filter has failed and is therefore emitting a greater amount of particulate matter than is allowed.

A typical particulate matter sensor uses a simple resistive device as the sensing element. The sensing element typically includes a non-conductive substrate, most often alumina or zirconia, and two conductive electrodes that may be made of a precious metal. The two electrodes may be formed in a pattern with inter-digitized fingers that maximizes the perimeter between the two electrodes. When the sensing element is disposed in the exhaust stream of a diesel engine, particulate matter will deposit thereupon and cause a high resistance short between the electrodes, thereby lowering the resistance between the two electrodes. The more particulate matter that is allowed to collect on the sensing element, the more the resistance between the two electrodes will decrease. The sensing element may be provided with a heater on the side opposite the electrodes in order to clean soot off of the electrodes when desired.

It is known to orient the sensing element of a particulate matter sensor such that the electrodes face toward the upstream end of the exhaust conduit. This allows particulate matter present in the exhaust gases to impinge on the sensing face and adhere thereto. One problem with this arrangement is that large particles that impinge the electrodes may create undesirable spikes in the output signal of the particulate matter sensor. Particles that impinge the sensing face may also adhere only temporarily to the electrodes due to high exhaust flow velocity, thereby producing an undesirable output signal from the particulate matter sensor.

It is also known to dispose a shield over the portion of the sensing element that extends into the exhaust conduit. The shield is provided with a plurality of passages that allow the exhaust gases to impinge the electrodes which face toward the upstream end of the exhaust conduit. One problem with shields of this configuration is that the portion of the shield between the plurality of passages masks or prevents the exhaust gasses from impinging on all areas of the electrodes, thereby rendering these masked areas unused and ineffective for sensing particulate matter. This shield configuration also does not address the unsatisfactory output signal that may result from large particulate matter impinging the sensing face. This shield configuration also does not address the problem of particles adhering only temporarily to the electrodes due to high exhaust flow velocity.

Another problem common to prior art particulate matter sensors is that the sensing element is not inserted far enough into the exhaust stream in order to reach the center of the exhaust conduit where the exhaust gas mixture is most likely to contain particulate matter regardless of the radial location of a failure in the diesel particulate filter. A minimum exhaust conduit length of 7 to 10 times its diameter may be needed to mix a stream of particulate matter so that the particulate matter is distributed across the entire diameter of the exhaust conduit. If the exhaust conduit is 90 mm in diameter and the particulate matter sensor is placed near the exhaust conduit wall at a position diametrically opposite the location of the failure in the diesel particulate filter, it could take almost 1 meter to mix a stream of particulate matter coming out of the diesel particulate filter in order for the particulate matter sensor to sense the particulate matter. Placement of the particulate matter sensor 1 meter from the diesel particulate filter may be undesirable, for example, because the length of the exhaust conduit may be less than 1 meter.

It has been found that simply inserting the sensing element further into the exhaust conduit in order to place the electrodes near the center of the exhaust conduit is not effective for sensing the particulate matter present in the exhaust gases because of shortfalls not present in a particulate matter sensor having a sensing element placed near the wall of the exhaust conduit. The length of the sensing element is limited by its strength. Therefore, if the sensing element is inserted far enough into the exhaust stream for its electrodes to be located near the center of the exhaust conduit, the sensing element will be disposed completely within the exhaust conduit. This will cause the sensing element to be the same temperature as the exhaust gases and therefore will have less of a tendency for particulate matter to adhere to the sensing element. A sensing element placed near the wall of the exhaust conduit will tend to have a temperature lower than the exhaust because a portion of the sensing element will extend to the cooler environment outside of the exhaust conduit and will pull heat out of the portion of sensing element that is located in the exhaust conduit. Due to the thermophoretic effect, the particulate matter that is at a higher temperature than the sensing element will have a tendency to adhere better to the cooler sensing element. However, a particulate matter sensor with a sensing element placed near the wall of the exhaust conduit has the deficiencies mentioned earlier.

What is needed is a particulate matter sensor that can effectively bring particulate matter from the center of the exhaust conduit, where the particulate matter is most likely to be present, to the sensing element located near the wall of the exhaust conduit where it can be sensed. What is also needed is a particulate matter sensor that is less effected by large particulate matter.

SUMMARY OF THE INVENTION

Briefly described, the present invention provides a particulate matter sensor for sensing particulate matter present in exhaust gasses flowing from an upstream end to a downstream end of an exhaust conduit for an internal combustion engine. The particulate matter sensor includes a sensing element with a sensing face that is configured to extend into the exhaust conduit. The sensing face is also configured to provide a signal indicative of an amount of particulate matter detected in the exhaust conduit. An inner shield surrounds the sensing face and has an inner shield inlet passage for admitting exhaust gases therein to be sensed by the sensing face. The inner shield also has an exit passage to allow exhaust gases to exit the inner shield. An outer shield surrounds a portion of the inner shied to define an outer shield chamber that extends axially beyond the inner shield and includes an outer shield inlet passage for communicating exhaust gases into the outer shield chamber from the upstream end of the exhaust conduit. Exhaust gases enter the inner shield from the outer shield inlet chamber.

BRIEF DESCRIPTION OF DRAWINGS

This invention will be further described with reference to the accompanying drawings in which.

DETAILED DESCRIPTION OF INVENTION

Figure 1:
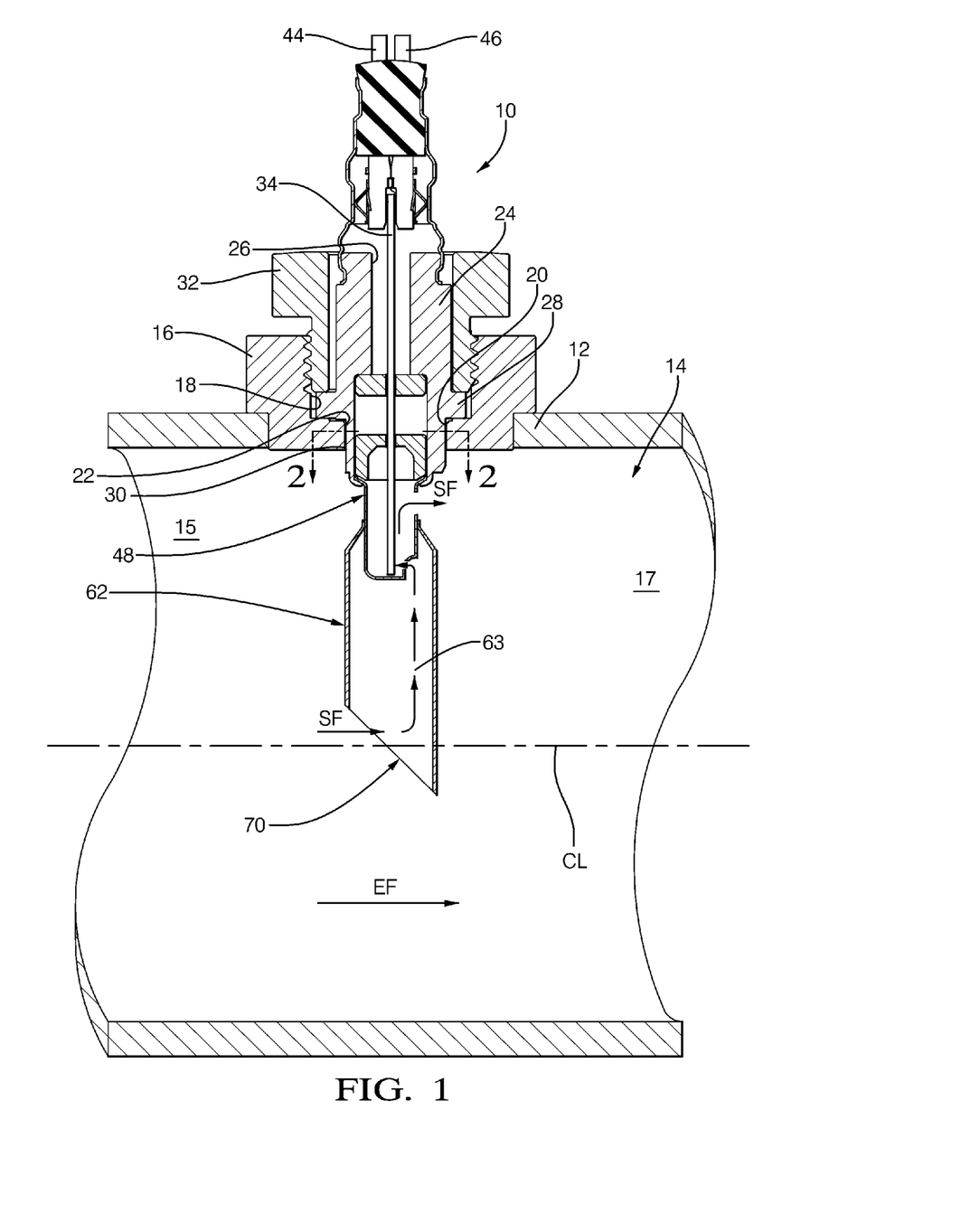
FIG. 1 is an axial cross-section of a particulate matter sensor in accordance with the present invention installed in an exhaust conduit.
Figure 2:
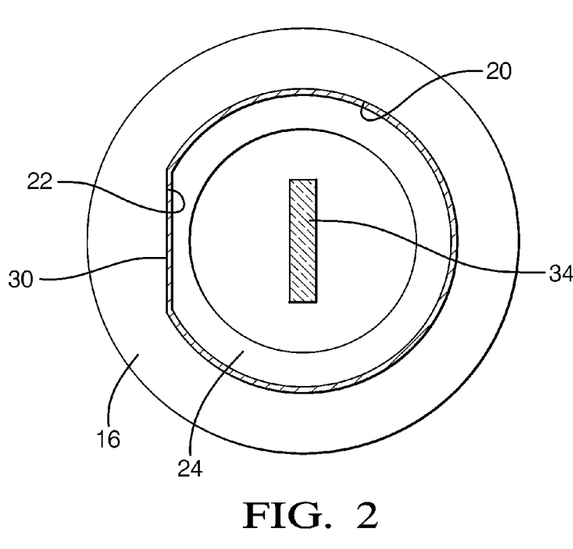
FIG. 2 is a radial cross-section of a particulate matter sensor in accordance with the present invention installed in a mounting boss of an exhaust conduit.

In accordance with a preferred embodiment of this invention and referring to FIG. 1, particulate matter sensor 10 is shown installed through exhaust conduit wall 12 of exhaust conduit 14 having upstream end 15 for receiving exhaust gases from an internal combustion engine (not shown) and downstream end 17 for communicating exhaust gases out of exhaust conduit 14 to the atmosphere. Exhaust conduit wall 12 includes mounting boss 16 extending therethrough for installing particulate matter sensor 10 therein. Mounting boss 16 includes stepped bore 18 for receiving particulate matter sensor 10 therein. Mounting boss 16 also includes through bore 20 extending from the bottom of stepped bore 18 to allow particulate matter sensor 10 to extend into the interior of exhaust conduit 14. Through bore 20 includes a locating feature such as mounting boss flat 22 (which is best viewed in FIG. 2) in order to radially orient particulate matter sensor 10 to exhaust conduit 14.

Particulate matter sensor 10 includes housing 24 with longitudinal bore 26 extending there through. Housing 24 includes radial flange 28 extending radially outward therefrom. Radial flange 28 axially and radially positions particulate matter sensor 10 within stepped bore 18 of mounting boss 16. Housing 24 also includes housing flat 30 that aligns with mounting boss flat 22 (which is best viewed in FIG. 2) in order to radially orient particulate matter sensor 10 to exhaust conduit 14.

Retainer nut 32 is threadably engaged with stepped bore 18 for retaining particulate matter sensor 10 to mounting boss 16. Radial flange 28 is axially captured between retainer nut 32 and stepped bore 18 such that when retainer nut 32 is tightened, particulate matter sensor 10 is securely held to mounting boss 16.

Figure 3:
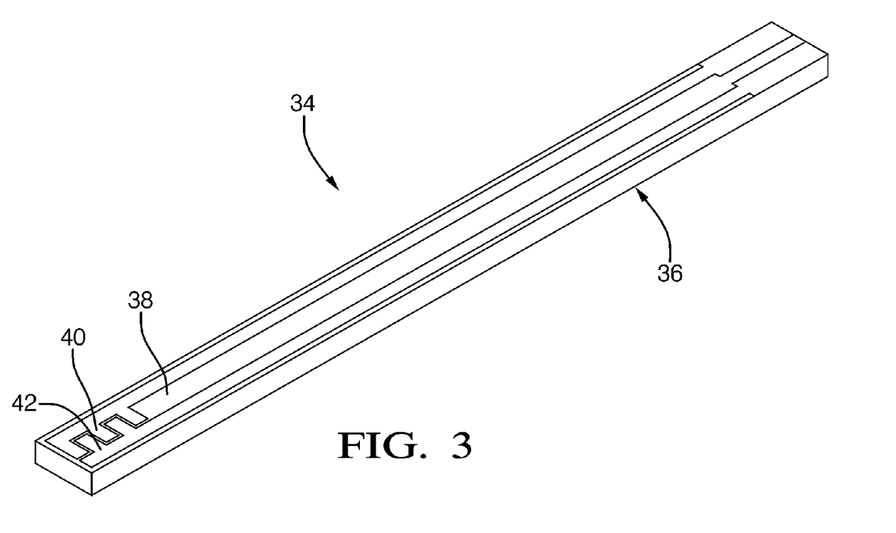
FIG. 3 is an isometric view of a sensing element for a particulate matter sensor in accordance with the present invention.

Now referring to FIGS. 1 and 3, sensing element 34 is disposed in longitudinal bore 26 and extends axially from particulate matter sensor 10 radially into exhaust conduit 14. Sensing element 34 also preferably extends radially outside exhaust conduit 14. Sensing element 34 includes a non-conductive substrate 36 with a sensing face 38 that is oriented in exhaust conduit 14 to be facing toward downstream end 17. First and second electrodes 40, 42 are disposed on sensing face 38 and are arranged to maximize the perimeter there between, for example, by forming a pattern of inter-digitized fingers although many different patterns may be used. Although not shown, a heating element may be disposed on the face opposite sensing face 38 in order to clean soot off first and second electrodes 40, 42 when desired. First and second electrodes 40, 42 are conductively connected to first and second lead wires 44, 46 which extend to an engine control module (not shown) to provide a signal thereto.

Figure 4:
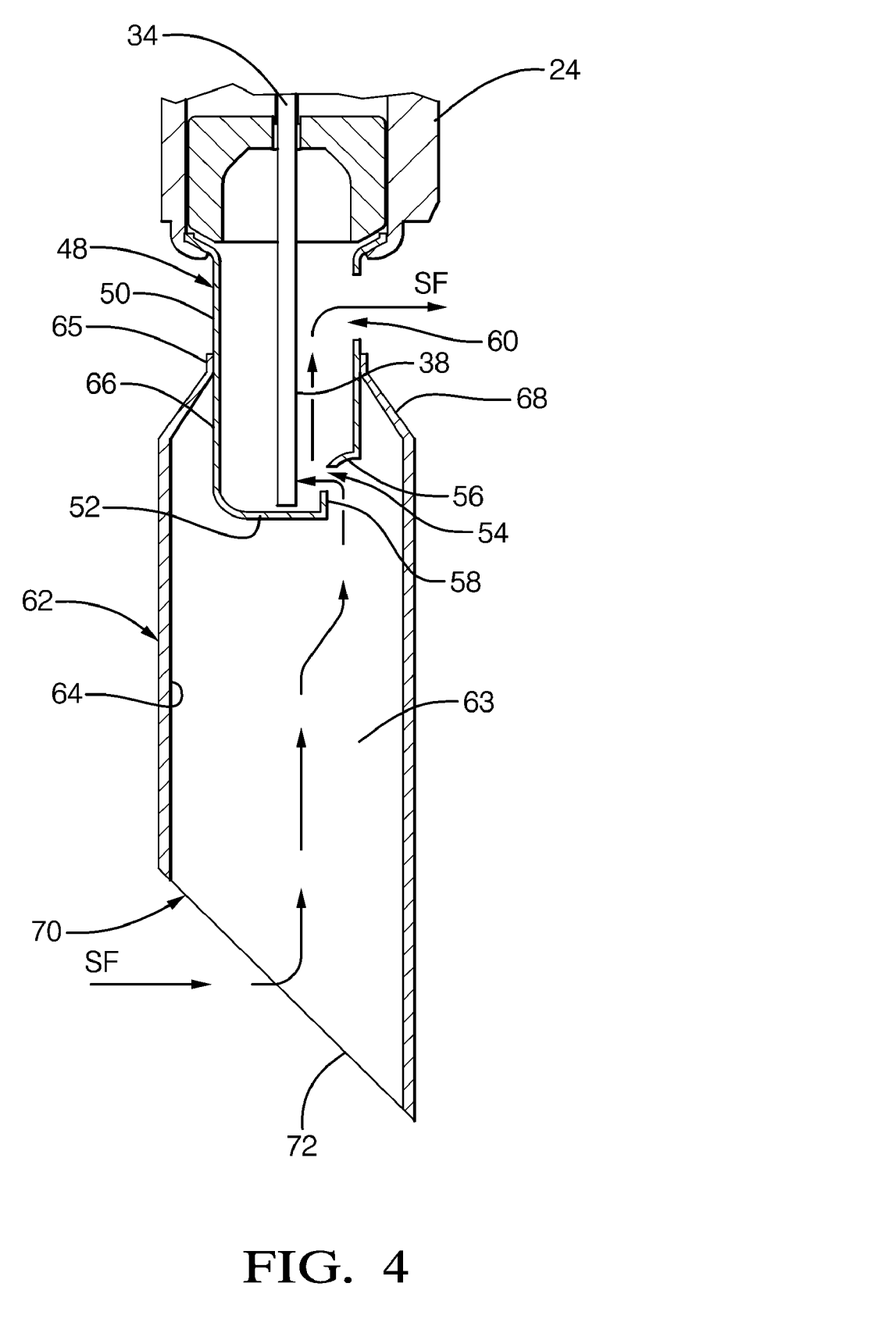
FIG. 4 is an axial cross section of an inner and outer shield arrangement for a particulate matter sensor in accordance with the present invention.

Now referring to FIGS. 1 and 4, inner shield 48 together with housing 24 substantially surround the portion of sensing element 34 that extends into exhaust conduit 14. Inner shield 48 includes inner shield side wall 50 that is substantially tubular. Inner shield 48 is attached at one end to housing 24 by crimping or welding, for example. The end of inner shield 48 opposite the end attached to housing 24 includes end cover 52 that may be of unitary construction with inner shield side wall 50 or may alternatively be made of a separate piece which is joined to inner shield side wall 50.

Inner shield inlet passage 54 is provided through inner shield side wall 50 for communicating exhaust gases into inner shield 48. Inner shield inlet passage 54 is oriented in exhaust conduit 14 to be facing toward downstream end 17, or in other words, inner shield inlet passage 54 is radially located through the portion of inner shield 48 that faces toward downstream end 17 which is the same direction that sensing face 38 is oriented. Sensing element 34 preferably extends axially into inner shield 48 to allow the distal end of sensing element 34 to be at least even with the portion of inner shield inlet passage 54 nearest housing 24 and more preferably, sensing element 34 extends axially further into inner shield 48 to allow the distal end of sensing element 34 to extend axially beyond the portion of inner shield inlet passage 54 nearest housing 24. Flow director 56 may be disposed at a portion of inner shield inlet passage 54 nearest housing 24 in order to direct incoming exhaust gases to impinge on sensing face 38. Flow director 56 extends from inner shield inlet passage 54 into inner shield 48. Barrier 58 may define the portion of inner shield inlet passage 54 distal from housing 24. Barrier 58 extends substantially axially away from end cover 52 to deter exhaust gases from flowing between the axial space formed between sensing element 34 and end cover 52 which could prevent impingement of exhaust gases on sensing face 38. Barrier 58 preferably extends axially a distance that is at least as much as the axial distance between sensing element 34 and end cover 52. While inner shield inlet passage 54 has been described as a single passage, it should now be understood that inner shield inlet passage 54 may also take the form of two or more individual inlet passages.

Inner shield 48 also includes exit passage 60 which is axially offset from inner shield inlet passage 54 toward housing 24 to allow exhaust gases to exit inner shield 48. Exit passage 60 is preferably oriented in exhaust conduit 14 to be facing toward downstream end 17, or in other words, exit passage 60 is preferably radially located through the portion of inner shield 48 that faces toward downstream end 17. However, exit passage 60 may be oriented as much as 90 degrees radially in either direction. Exit passage 60 is preferably sized to provide a flow area greater than or equal to the flow area provided by inner shield inlet passage 54. By sizing exit passage 60 in this way, a vacuum can be created to aid in pulling exhaust gases out of inner shield 48, thereby causing a large amount of exhaust gasses to be directed toward sensing face 38. While exit passage 60 has been described as a single passage, it should now be understood that exit passage 60 may also take the form of two or more individual exit passages.

Outer shield 62 is disposed over a portion of inner shield 48 to create outer shield chamber 63 extending axially beyond inner shield 48. Outer shield 62 has inner diameter 64 that is preferably greater than or equal to outer diameter 66 of inner shield 48 and includes attachment end 65 that is attached to outer diameter 66 of inner shield 48 at an axial location on inner shield 48 between inner shield inlet passage 54 and exit passage 60. When inner diameter 64 of outer shield 62 is greater than outer diameter 66 of inner shield, outer shield 62 includes reducing section 68 that reduces to the same diameter as outer diameter 66 to facilitate attachment of outer shield 62 to inner shield 48. It is also possible to reduce a portion of outer diameter 66 to receive outer shield 62 such that outer diameter 66 is the same as the outer diameter of outer shield 62. Outer shield 62 may be attached to inner shield 48 by crimping or welding, for example.

Outer shield 62 includes outer shield inlet passage 70 for communicating exhaust gases into outer shield chamber 63 from exhaust conduit 14. Outer shield inlet passage 70 is formed at inlet end 72 of outer shield 62 which is opposite attachment end 65 in order to allow exhaust gases near the center of exhaust conduit 14 to enter outer shield 62. Outer shield inlet passage 70 is formed to be substantially larger than inner shield inlet passage 54 and exit passage 60 in order to funnel a large amount of exhaust gases toward inner shield inlet passage 54. Outer shield inlet passage 70 is oriented in exhaust conduit 14 to be facing toward upstream end 15, or in other words, outer shield inlet passage is radially located through the portion of outer shield 62 that faces toward upstream end 15 which is the radial opposite direction that sensing face 38 and inner shield inlet passage 54 are oriented. Outer shield inlet passage 70 may be formed by cutting outer shield at a diagonal, for example, at a 45° or 60° angle with respect to the horizontal as shown in FIG. 1. When particulate matter sensor 10 is assembled to exhaust conduit 14, the axial center of outer shield inlet passage 70 is preferably inserted to be near the diametric center of exhaust conduit 14. The axial center of outer shield inlet passage 70 is preferably offset from the diametric center of exhaust conduit 14 by no more than 20 percent of the diameter of exhaust conduit 14 and more preferably by no more than 10 percent. The diametric center of exhaust conduit 14 may additionally or alternatively fall within outer shield inlet passage 70. In FIG. 1, the axial center of outer shield inlet passage 70 and the diametric center of exhaust conduit 14 are shown as coinciding and are designated by line CL.

Figure 5:
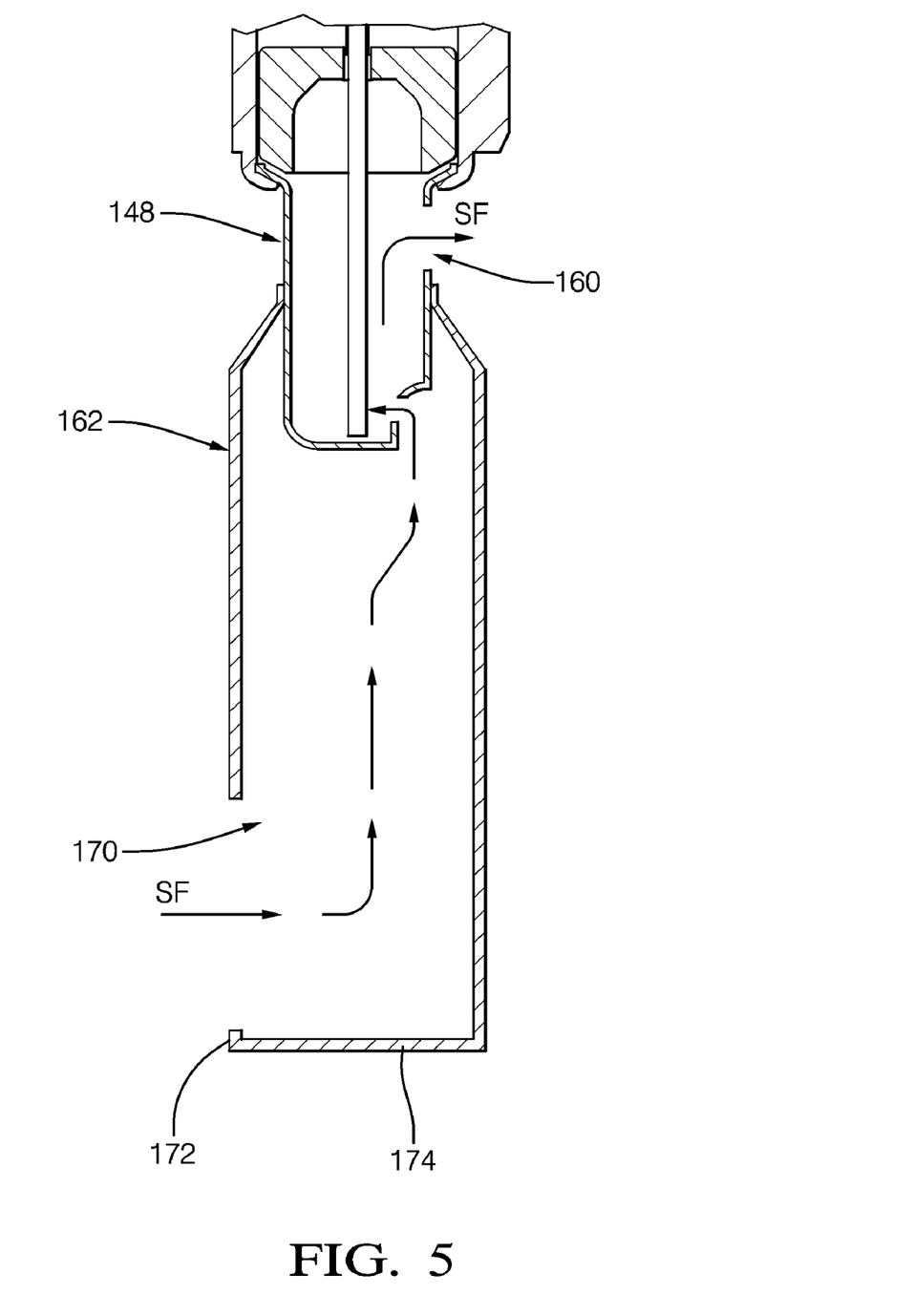
FIG. 5 is an axial cross section of a second embodiment of an inner and outer shield arrangement for a particulate matter sensor in accordance with the present invention.

Now referring to FIG. 5, alternative embodiment outer shield 162 is shown. Outer shield 162 is the same as outer shield 62 shown in FIGS. 1 and 4 with the exception of outer shield inlet passage 170. Outer shield inlet passage 170 is formed by removing a radial section of outer shield 162 at inlet end 172. In this embodiment, outer shield 162 also includes inlet end cover 174 which covers inlet end 172. The orientation and sizing of outer shield inlet passage 170 is the same as that described for outer shield inlet passage 70. While outer shield inlet passage 170 has been described as a single passage, it should now be understood that outer shield inlet passage 170 may also take the form of two or more individual inlet passages.

Figure 6:
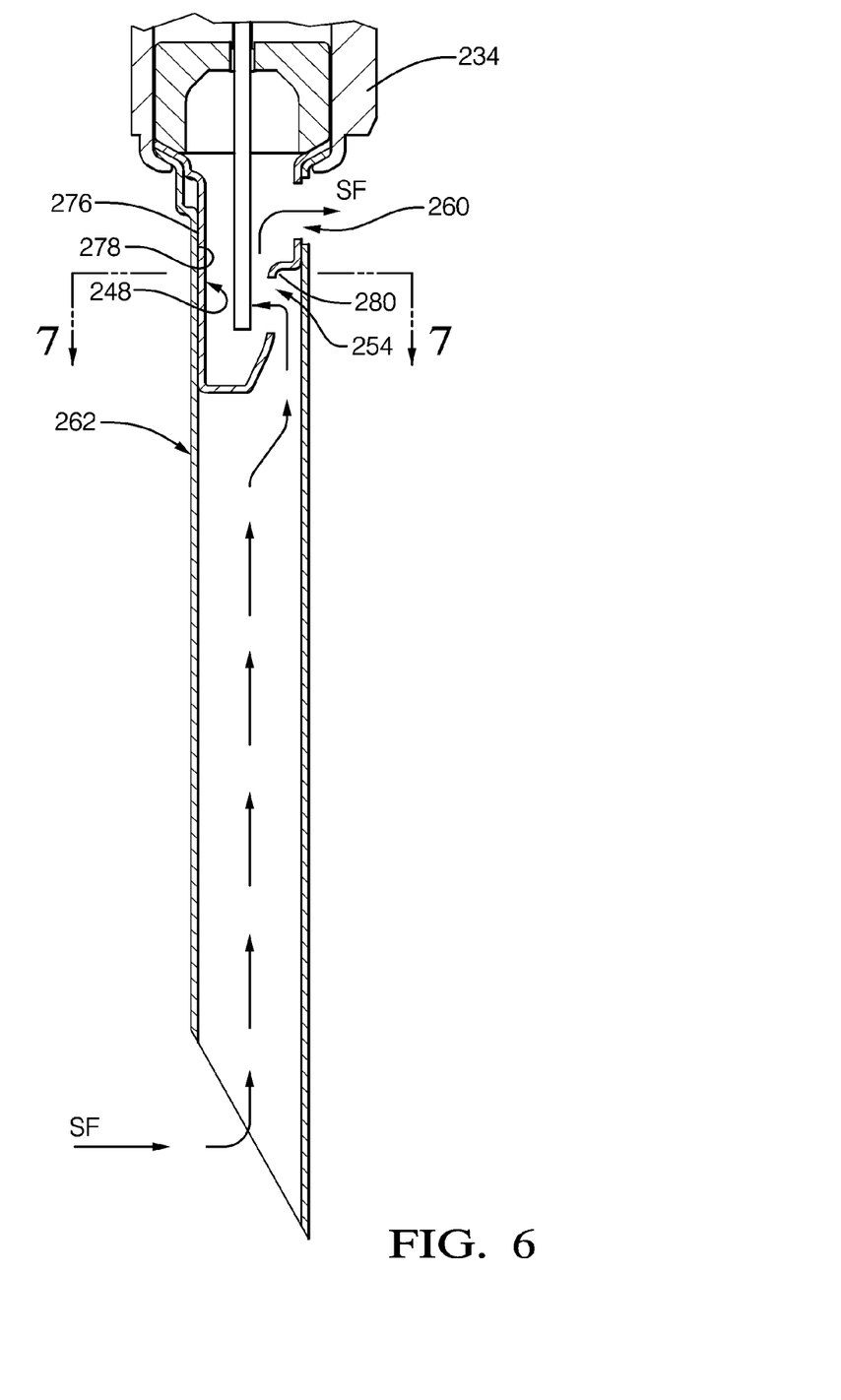
FIG. 6 is an axial cross section of a third embodiment of an inner and outer shield arrangement for a particulate matter sensor in accordance with the present invention.
Figure 7:
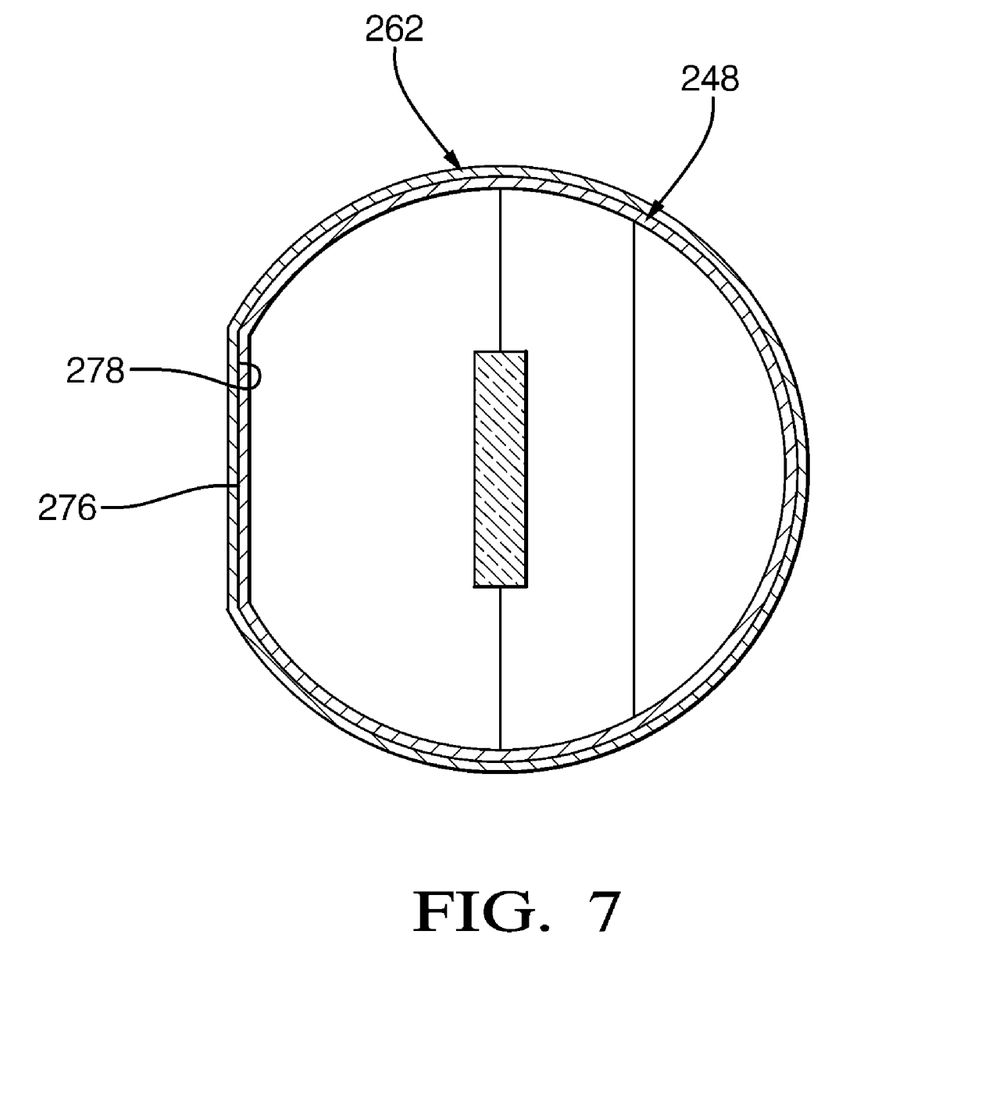
FIG. 7 is a radial cross section through the inner and outer shield of the third embodiment of an inner and outer shield arrangement for a particulate matter sensor in accordance with the present invention.

Now referring to FIGS. 6 and 7, alternative embodiment inner shield 248 and outer shield 262 are shown. In this embodiment, inner shield 248 is attached to outer shield 262 by press fit. Both inner shield 248 and outer shield 262 may then be crimped to housing 224 simultaneously. Since inner shield 248 is press fit to outer shield 262 and both are crimped to housing 224, exit passage 260 is formed through both inner shield 248 and outer shield 262. A portion of inner shield 248 may be radially inset to form step 280 in order provide radial clear between outer shield 262 and thereby allow exhaust gas flow to enter inner shield inlet passage 254.

Inner shield 248 may include an inner shield orientation feature, for example, inner shield flat 276. Outer shield 262 may include a corresponding outer shield orientation feature, for example, outer shield flat 278 to interface with inner shield flat 276. In this way inner, shield 248 and outer shield 262 may be radially oriented to each other during assembly.

The tortuous path created by having outer shield inlet passage 70, 170, 270 facing toward upstream end 15 while inner shield inlet passage 54 and sensing face 38 face downstream end 17 inhibits large particulate matter from impinging sensing face 38. Since large particulate matter is inhibited from impinging sensing face 38, an output signal that is smoother will be produced by particulate matter sensor 10.

In operation, and referring to FIGS. 1 and 4, exhaust gases flow through exhaust conduit 14 in the direction of arrow EF from upstream end 15 to downstream end 17. A portion of the exhaust gas flow, sensing flow indicated as arrow SF, enters outer shield chamber 63 of outer shield 62 through outer shield inlet passage 70 which faces toward upstream end of exhaust conduit 14. The sensing flow enters inner shield 48 from outer shield chamber 63. Similarly, the sensing flow may only able to exit outer shield chamber 63 by entering inner shield 48 through inner shield inlet passage 54. As the sensing flow enters inner shield 48 through inner shield inlet passage 54, it is guided by flow director 56 to impinge on sensing face 38 where particulate matter present in the sensing flow will adhere thereto and cause a change in resistance between first and second electrodes 40, 42. After impinging on sensing face 38, the sensing flow will exit inner shield 48 through exit passage 60 where the sensing flow combines with the exhaust gas flow in exhaust conduit 14. As can be seen in each of the embodiments (FIGS. 1, 4, 5, and 6), the sensing flow exiting through exit passage 60, 160, 260 does not re-enter outer shield chamber 63, 163, 263 before being communicated back into the exhaust conduit. In other words, the sensing flow is communicated directly to the exhaust conduit from inner shield 48, 148, 248.

Although not shown, a drain hole may be provided through inner shield 48, for example, through end cover 52. The drain hole allows moisture that may condense within inner shield 48 to drain therefrom. The drain hole may be sufficiently small such that an insignificant flow of exhaust gas may enter or exit inner shield 48 through the drain hole. This insignificant flow of exhaust gas is anticipated while still considering the sensing flow to enter inner shield 48 through inner shield inlet passage 54 and exit inner shield 48 through exit passage 60.

Although not shown, the outer shield inlet passage may be formed in other orientations. For example, the outer shield may be formed by having the outer shield cut substantially square and thereby the inlet passage may not face toward upstream end 15. This may be less effective than the embodiments previously discussed, but may be effective enough to provide a sampling of exhaust gasses near the center of the exhaust conduit to provide a signal indicative of an amount of particulate matter in the exhaust conduit.

While this invention has been described in terms of preferred embodiments thereof, it is not intended to be so limited, but rather only to the extent set forth in the claims that follow.

I claim:

1. A particulate matter sensor for sensing particulate matter present in exhaust gasses flowing from an upstream end to a downstream end of an exhaust conduit for an internal combustion engine, said particulate matter sensor comprising:
a sensing element with a sensing face, said sensing face configured to extend into said exhaust conduit, and further configured to provide a signal indicative of an amount of particulate matter detected in said exhaust conduit;
an inner shield surrounding said sensing face and having an inner shield inlet passage for admitting exhaust gases into said inner shield to be sensed by said sensing face, said inner shield also having an exit passage to allow exhaust gases to exit said inner shield; and
an outer shield surrounding a portion of said inner shield to define an outer shield chamber extending axially beyond said inner shield, said outer shield having an outer shield inlet passage configured for communicating exhaust gases into said outer shield chamber from said upstream end of said exhaust conduit, wherein exhaust gases enter said inner shield from said outer shield chamber.

2. A particulate matter sensor as in claim 1, wherein exhaust gases enter said inner shield only from said outer shield chamber.

3. A particulate matter sensor as in claim 1, wherein exhaust gases flow out of said outer shield chamber only through said inner shield inlet passage.

4. A particulate matter sensor as in claim 1, wherein said sensing face is configured to face toward said downstream end of said exhaust conduit.

5. A particulate matter sensor as in claim 4, wherein said inner shield inlet passage is configured to face toward said downstream end of said exhaust conduit.

6. A particulate matter sensor as in claim 1, wherein said exit passage is configured to face toward said downstream end of said exhaust conduit.

7. A particulate matter sensor as in claim 1, wherein said exit passage is configured to communicate exhaust gases directly to said exhaust conduit from said inner shield.

8. A particulate matter sensor as in claim 1, wherein said outer shield inlet passage is configured to face toward said upstream end of said exhaust conduit.

9. A particulate matter sensor as in claim 1, wherein said outer shield inlet passage is sized to be substantially larger than said inner shield inlet passage.

10. A particulate matter sensor as in claim 1 further comprising a locating feature to radially orient said particulate matter sensor in a mounting boss of said exhaust conduit.

11. A particulate matter sensor as in claim 1, wherein said inner shield inlet passage includes a flow director extending therefrom into said inner shield for directing exhaust gases to impinge on said sensing face.

12. A particulate matter sensor as in claim 1, wherein said inner shield inlet passage is axially offset from said exit passage.

13. A particulate matter sensor as in claim 12, wherein said outer shield is attached to the perimeter of said inner shield at a location axially between said inner shield inlet passage and said exit passage.

14. A particulate matter sensor as in claim 1, wherein said sensing element is configured to extend to the exterior of said exhaust conduit.

15. A particulate matter sensor as in claim 1, wherein said inner shield has an inner shield orientation feature that cooperates with an outer shield orientation feature of said outer shield to radially orient said inner shield with said outer shield.

16. An exhaust system for an internal combustion engine, said exhaust system having an exhaust conduit with an upstream end, a downstream end, and a particulate matter sensor for sensing particulate matter present in exhaust gasses flowing from said upstream end to said downstream, wherein said particulate matter sensor comprises:
a sensing element with a sensing face extending into said exhaust conduit and configured to provide a signal indicative of an amount of particulate matter detected in said exhaust conduit;
an inner shield surrounding said sensing face and having an inner shield inlet passage for admitting exhaust gases into said inner shield to be sensed by said sensing face, said inner shield also having an exit passage to allow exhaust gases to exit said inner shield;
an outer shield surrounding a portion of said inner shield to define an outer shield chamber extending axially beyond said inner shield, said outer shield having an outer shield inlet passage for communicating exhaust gases into said outer shield chamber from said upstream end of said exhaust conduit, wherein exhaust gases enter said inner shield from said outer shield chamber.

17. An exhaust system as in claim 16, wherein exhaust gases enter said inner shield only from said outer shield chamber.

18. An exhaust system as in claim 16, wherein exhaust gases flow out of said outer shield chamber only through said inner shield inlet passage.

19. An exhaust system as in claim 16, wherein said sensing face faces toward said downstream end of said exhaust conduit.

20. An exhaust system as in claim 19, wherein said inner shield inlet passage faces toward said downstream end of said exhaust conduit.

21. An exhaust system as in claim 16, wherein said exit passage faces toward said downstream end of said exhaust conduit.

22. An exhaust system as in claim 16, wherein said exit passage communicates exhaust gases directly to said exhaust conduit from said inner shield.

23. An exhaust system as in claim 16, wherein said outer shield inlet passage faces toward said upstream end of said exhaust conduit.

24. An exhaust system as in claim 16, wherein said outer shield inlet passage is sized to be substantially larger than said inner shield inlet passage.

25. An exhaust system as in claim 16, wherein said particulate matter sensor further comprises a locating feature to radially orient said particulate matter sensor in a mounting boss of said exhaust conduit.

26. An exhaust system as in claim 16, wherein said inner shield inlet passage includes a flow director extending therefrom into said inner shield for directing exhaust gases to impinge on said sensing face.

27. An exhaust system as in claim 16, wherein said inner shield inlet passage is axially offset from said exit passage.

28. An exhaust system as in claim 27, wherein said outer shield is attached to the perimeter of said inner shield at a location axially between said inner shield inlet passage and said exit passage.

29. An exhaust system as in claim 16, wherein said sensing element extends to the exterior of said exhaust conduit.

30. An exhaust system as in claim 16 wherein said inner shield has an inner shield orientation feature that cooperates with an outer shield orientation feature of said outer shield to radially orient said inner shield with said outer shield.

31. An exhaust system as in claim 16, wherein the axial center of said outer shield inlet passage is offset from the diametric center of said exhaust conduit by no more than 20 percent of the diameter of the exhaust conduit.

32. An exhaust system as in claim 31, wherein the axial center of said outer shield inlet passage is offset from the diametric center of said exhaust conduit by no more than 10 percent of the diameter of the exhaust conduit.

33. An exhaust system as in claim 16, wherein the diametric center of said exhaust conduit falls within said outer shield inlet passage.

* * * * *